United States Patent
Blasco et al.

(10) Patent No.: US 7,094,894 B2
(45) Date of Patent: Aug. 22, 2006

(54) FUNGICIDAL TRIAZOLOPYRIMIDINES, METHOD FOR THE PRODUCTION THEREOF, USE THEREOF FOR CONTROLLING HARMFUL FUNGI, AND AGENTS CONTAINING SAID FUNGICIDAL TRIAZOLOPYRIMIDINES

(75) Inventors: Jordi Tormo i Blasco, Laudenbach (DE); Carsten Blettner, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Peter Schäfer, Ottersheim (DE); Frank Schieweck, Hessheim (DE); Anja Schwögler, Mannheim (DE); Eberhard Ammermann, Heppenheim (DE); Siegfried Strathmann, Limburgerhof (DE); Gisela Lorenz, Neustadt (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/513,030

(22) PCT Filed: Apr. 30, 2003

(86) PCT No.: PCT/EP03/04498

§ 371 (c)(1),
(2), (4) Date: Nov. 1, 2004

(87) PCT Pub. No.: WO03/093271

PCT Pub. Date: Nov. 13, 2003

(65) Prior Publication Data

US 2005/0256138 A1    Nov. 17, 2005

(30) Foreign Application Priority Data

May 3, 2002    (DE) ............... 102 19 992

(51) Int. Cl.
*C07D 487/04*    (2006.01)
*A01N 43/90*    (2006.01)
*C07C 69/618*    (2006.01)

(52) U.S. Cl. .......... 544/263; 514/259.31; 560/51; 560/82

(58) Field of Classification Search .......... 514/259.31; 544/263; 560/51, 82
See application file for complete search history.

(56) References Cited

U.S. PATENT DOCUMENTS

| 5,593,996 A | 1/1997 | Pees et al. ......... 514/259.31 |
| 6,316,486 B1 | 11/2001 | Lieb et al. ............ 514/411 |

FOREIGN PATENT DOCUMENTS

| FR | 2 765 875 | 1/1999 |
| GB | 2 355 261 | 4/2001 |
| WO | 01/17972 | 3/2001 |

*Primary Examiner*—Thomas C. McKenzie
(74) *Attorney, Agent, or Firm*—Novak Druce & Quigg, LLP; Jason D. Voight

(57) ABSTRACT

Disclosed are a method for producing fungicidal triazolopyrimidine compounds, agents containing said compounds, and the use thereof for controlling harmful fungi. Also disclosed are triazolopyrimidines of formula (I), in which the substituents have the following meaning: $L^1$ represents alkyl; $L^2$ represents halogen; $L^3$ represents hydrogen or halogen; X represents halogen, cyano, alkyl, alkoxy, or haloalkoxy; $R^1$, $R^2$ represent hydrogen, alkyl, haloalkyl, cycloalkyl, alkenyl, alkadienyl, alkinyl, or cycloalkinyl, phenyl, naphthyl, or a five-unit to ten-unit saturated, partially unsaturated, or aromatic heterocycle containing one to four heteroatoms from the group O, N, or S, $R^1$ and $R^2$ can also form a five-unit or six-unit ring along with the nitrogen atom to which they are linked. Said ring can be interrupted and/or substituted by an atom from the group O, N, and S while $R^1$ and/or $R^2$ can be substituted according to the description. The invention also relates to methods and intermediate products for producing said compounds, agents containing said compounds, and the use thereof for controlling harmful fungi

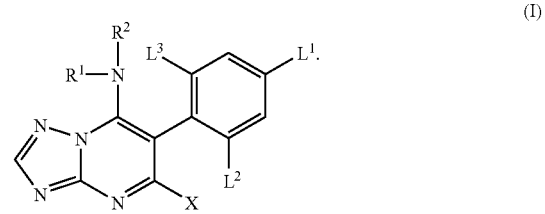

(I)

8 Claims, No Drawings

FUNGICIDAL TRIAZOLOPYRIMIDINES, METHOD FOR THE PRODUCTION THEREOF, USE THEREOF FOR CONTROLLING HARMFUL FUNGI, AND AGENTS CONTAINING SAID FUNGICIDAL TRIAZOLOPYRIMIDINES

The present invention relates to triazolopyrimidines of the formula I,

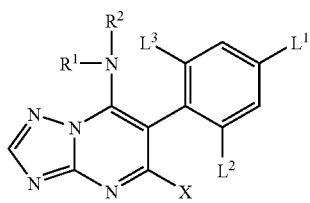

in which the substituents have the following meanings:

$L^1$ is $C_1$–$C_4$-alkyl;

$L^2$ is halogen;

$L^3$ is hydrogen or halogen;

X is halogen, cyano, $C_1$–$C_4$-alkyl, $C_1$–$C_4$-alkoxy or $C_1$–$C_2$-haloalkoxy;

$R^1$,$R^2$ are, independently of one another, hydrogen, $C_1$–$C_3$-alkyl, $C_1$–$C_{10}$-haloalkyl, $C_3$–$C_8$-cycloalkyl, $C_2$–$C_{10}$-alkenyl, $C_4$–$C_{10}$-alkadienyl, $C_2$–$C_{10}$-alkynyl or $C_4$–$C_{10}$-alkyl, which has no center of chirality, or $C_3$–$C_6$-cycloalkynyl, phenyl, naphthyl, or a five- to ten-membered saturated, partially unsaturated or aromatic heterocycle, containing one to four heteroatoms from the group consisting of O, N and S, $R^1$ and $R^2$ can also, together with the nitrogen atom to which they are bonded, form a five- or six-membered ring which can be interrupted by an atom from the group consisting of O, N and S and/or can carry one or more substituents from the group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1$–$C_4$-alkylene chain;

wherein $R^1$ and/or $R^2$ can be substituted by one to three identical or different groups $R^a$:

$R^a$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di($C_1$–$C_6$-alkyl)amino, $C_2$–$C_6$-alkenyl, $C_2$–$C_6$-alkenyloxy, $C_3$–$C_6$-alkynyloxy, $C_3$–$C_6$-cycloalkyl, phenyl, naphthyl or a five- to ten-membered saturated, partially unsaturated or aromatic heterocycle, containing one to four heteroatoms from the group consisting of O, N and S, wherein these aliphatic, alicyclic or aromatic groups, for their part, can be partially or completely halogenated or can carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl or dialkylaminothiocarbonyl, wherein the alkyl groups in these radicals contain 1 to 6 carbon atoms and the alkenyl or alkynyl groups mentioned in these radicals contain 2 to 8 carbon atoms;

and/or one to three of the following radicals:

cycloalkyl, cycloalkoxy, heterocyclyl or heterocyclyloxy, wherein the cyclic systems contain 3 to 10 ring members; aryl, aryloxy, arylthio, aryl-$C_1$–$C_6$-alkoxy, aryl-$C_1$–$C_6$-alkyl, hetaryl, hetaryloxy or hetarylthio, wherein the aryl radicals preferably contain 6 to 10 ring members and the hetaryl radicals contain 5 or 6 ring members, wherein the cyclic systems can be partially or completely halogenated or can be substituted by alkyl or haloalkyl groups.

The invention relates in addition to processes for and intermediates in the preparation of these compounds, compositions comprising them and their use in the control of harmful fungi.

Individual 6-(4-alkylphenyl)triazolopyrimidines are known from EP-A 71 792 and EP-A 550 113. WO-A 98/46608 discloses 5-chlorotriazolopyrimidines with 7-haloalkylamino groups, in the course of which generically including corresponding 6-(4-alkylphenyl)triazolopyrimidines. The compounds described in the documents mentioned are known for the control of harmful fungi.

However, in many cases, their action is unsatisfactory. It is an object of the present invention, taking this as its starting point, to provide compounds with an improved action and/or a broadened spectrum of activity.

We have found that this object is achieved with the compounds defined at the start. Processes for and intermediates in their preparation, compositions comprising them and processes for the control of harmful fungi through the use of the compounds I have also been found.

The compounds of the formula I are distinguished from those from the abovementioned documents in the substitution of the 6-(4-alkylphenyl) group, which additionally carries a halogen atom in the 2-position.

The compounds of the formula I have, in comparison with the known compounds, an increased activity against harmful fungi.

The compounds according to the invention can be obtained in various ways. They are advantageously prepared by reaction of 5-aminotriazole of the formula II with appropriately substituted phenylmalonates of the formula III in which R is alkyl, preferably $C_1$–$C_6$-alkyl, in particular methyl or ethyl.

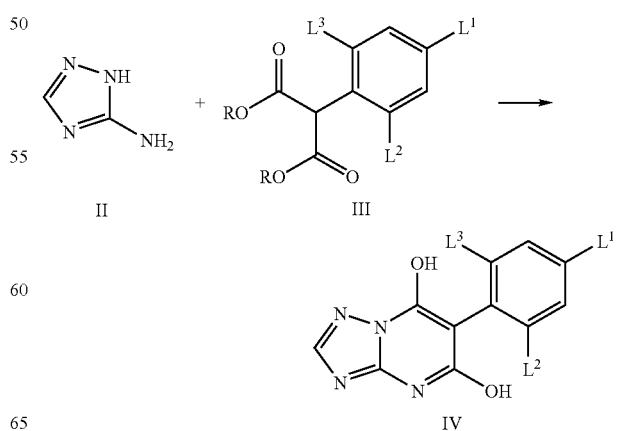

This reaction is usually carried out at temperatures of 80° C. to 250° C., preferably 120° C. to 180° C., without solvent or in an inert organic solvent, in the presence of a base [cf. EP-A 770 615] or in the presence of acetic acid under the conditions known from Adv. Het. Chem., Vol. 57, pp. 81 ff. (1993).

Suitable solvents are aliphatic hydrocarbons, aromatic hydrocarbons, such as toluene or o-, m- and p-xylene, halogenated hydrocarbons, ethers, nitriles, ketones, alcohols, N-methylpyrrolidone, dimethyl sulfoxide, dimethylformamide and dimethylacetamide. In a particularly preferred way, the reaction is carried out without solvent or in chlorobenzene, xylene, dimethyl sulfoxide, N-methylpyrrolidone. Mixtures of the solvents mentioned can also be used.

Suitable bases are generally inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates, alkali metal hydrogencarbonates, or organometallic compounds, in particular alkali metal alkyls, alkyl magnesium halides, and alkali metal and alkaline earth metal alkoxides and magnesium dimethoxide, as well as organic bases, e.g. tertiary amines, such as trimethylamine, triethylamine, triisopropylethylamine, tributylamine, N-methylpiperidine and N-methylmorpholine, pyridine, substituted pyridines, such as collidine, lutidine and 4-dimethylaminopyridine, and bicyclic amines. Tertiary amines, such as triisopropylethylamine, tributylamine, N-methylmorpholine or N-methylpiperidine, are especially preferred.

The bases are generally used in catalytic amounts. However, they can also be used in equimolar amounts, in excess or possibly as solvent.

The starting materials are generally reacted with one another in equimolar amounts. It can be advantageous to the yield to use the base and the malonate III in an excess with respect to the triazole.

Phenylmalonates of the formula III are advantageously obtained from the reaction of suitably substituted bromobenzenes with dialkyl malonates under Cu(I) catalysis [cf. Chemistry Letters, pp. 367–370, 1981; EP-A 10 02 788].

The dihydroxytriazolopyrimidines of the formula IV are converted to the dihalopyrimidines of the formula V under the conditions known from WO-A 94/20501. A chlorinating agent or a brominating agent, such as phosphorus oxybromide or phosphorus oxychloride, optionally in the presence of a solvent, is advantageously used as halogenating agent.

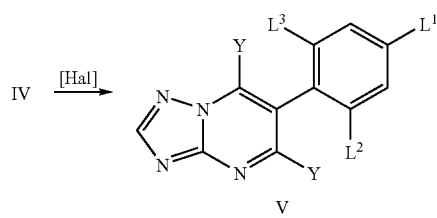

This reaction is usually carried out at 0° C. to 150° C., preferably at 80° C. to 125° C. [cf. EP-A 770 615].

Dihalopyrimidines of the formula V are further reacted with amines of the formula VI,

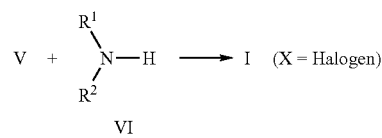

in which $R^1$ and $R^2$ are defined as in formula I, to give compounds of the formula I in which X is halogen.

This reaction is advantageously carried out at 0° C. to 70° C., preferably 10° C. to 35° C., preferably in the presence of an inert solvent, such as ethers, e.g. dioxane, diethyl ether or, particularly, tetrahydrofuran, halogenated hydrocarbons, such as dichloromethane, and aromatic hydrocarbons, such as, for example, toluene [cf. WO-A 98/46608].

The use of a base, such as tertiary amines, for example triethylamine, or inorganic amines, such as calcium carbonate, is preferred; in addition, excess amine of the formula VI can be used as a base.

Compounds of the formula I in which X represents cyano, $C_1$–$C_6$-alkoxy or $C_1$–$C_2$-haloalkoxy can advantageously be obtained from the reaction of compounds I, in which X represents halogen, preferably chlorine, with compounds M-X' (formula VII). Compounds VII represent, depending on the meaning of the group X' to be introduced, an inorganic cyanide, an alkoxide or a haloalkoxide. The reaction is advantageously carried out in the presence of an inert solvent. The cation M in formula VII is of little importance; for practical reasons, ammonium, tetraalkylammonium, alkali metal or alkaline earth metal salts are usually preferred.

The reaction temperature usually lies between 0 and 120° C., preferably between 10 and 40° C. [cf. J. Heterocycl. Chem., Vol. 12, pp. 861–863 (1975)].

Suitable solvents include ethers, such as dioxane, diethyl ether and, preferably, tetrahydrofuran, halogenated hydrocarbons, such as dichloromethane, and aromatic hydrocarbons, such as toluene.

Compounds of the formula I in which X is $C_1$–$C_4$-alkyl can advantageously be obtained through the following synthetic route:

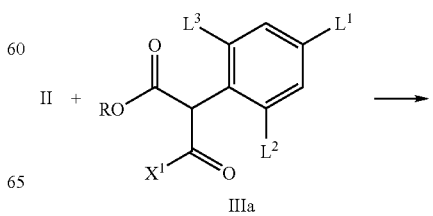

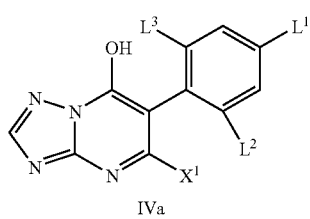

The 5-alkyl-7-hydroxy-6-phenyltriazolopyrimidines IVa are obtained from the diketones IIIa. The 5-methyl-7-hydroxy-6-phenyltriazolopyrimidines are obtained through the use of the readily accessible 2-phenylacetoacetic esters (IIIa with $X^1=CH_3$) [cf. Chem. Pharm. Bull., 9, 801, (1961)]. The preparation of the starting compounds IIIa is advantageously carried out under the conditions described in EP-A 10 02 788.

The 5-alkyl-7-hydroxy-6-phenyltriazolopyrimidines obtained in this way are reacted with halogenating agents to give the 7-halotriazolopyrimidines of the formula Va. Chlorinating or brominating agents, such as phosphorus oxybromide, phosphorus oxychloride, thionyl chloride, thionyl bromide or sulfuryl chloride, are preferably used. The reaction can be carried out in bulk or in the presence of a solvent. Usual reaction temperatures are from 0 to 150° C. or, preferably, from 80 to 125° C.

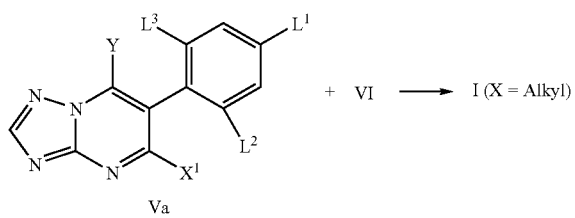

The reaction of Va with amines VI is carried out under the conditions described further above.

Compounds of the formula I in which X represents $C_1$–$C_4$-alkyl can alternatively also be prepared from compounds I in which X represents halogen, in particular chlorine, and malonates of the formula VIII. In formula VIII, X" represents hydrogen or $C_1$–$C_3$-alkyl and R represents $C_1$–$C_4$-alkyl. They are reacted to give compounds of the formula IX and are decarboxylated to give compounds I [cf. U.S. Pat. No. 5,994,360].

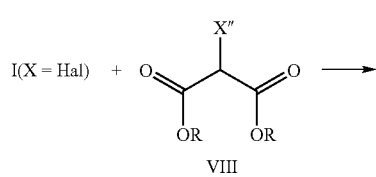

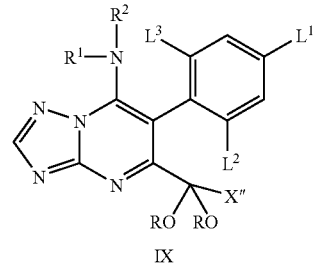

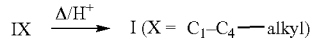

The malonates VIII are known in the literature [J. Am. Chem. Soc., Vol. 64, 2714 (1942); J. Org. Chem., Vol. 39, 2172 (1974); Helv. Chim. Acta, Vol. 61, 1565 (1978)] or can be prepared according to the literature cited.

The subsequent saponification of the ester IX is carried out under generally standard conditions. Depending on the various structural components, the alkaline or the acidic saponification of the compounds IX may be advantageous. Under the conditions of the saponification of esters, the decarboxylation to give I may already take place, completely or partially.

The decarboxylation usually takes place at temperatures of 20° C. to 180° C., preferably 50° C. to 120° C., in an inert solvent, optionally in the presence of an acid.

Suitable acids are hydrochloric acid, sulfuric acid, phosphoric acid, formic acid, acetic acid and p-toluenesulfonic acid. Suitable solvents are water, aliphatic hydrocarbons, such as pentane, hexane, cyclohexane and petroleum ether, aromatic hydrocarbons, such as toluene and o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, dimethyl sulfoxide, dimethylformamide and dimethylacetamide. In a particularly preferred way, the reaction is carried out in hydrochloric acid or acetic acid. Mixtures of the solvents mentioned can also be used.

Compounds of the formula I in which X is $C_1$–$C_4$-alkyl can also be obtained by coupling of 5-halotriazolopyrimidines of the formula I in which X represents halogen with organometallic reagents of the formula X. In an embodiment of this process, the reaction is carried out under transition metal catalysis, such as Ni or Pd catalysis.

In formula X, M is a metal ion with a valency of Y, such as, for example, B, Zn or Sn. This reaction can be carried out, for example, analogously to the following methods: J. Chem. Soc. Perkin Trans., 1, 1187 (1994), ibid., 1, 2345 (1996); WO-A 99/41255; Aust. J. Chem., Vol. 43, 733

(1990); J. Org. Chem., Vol. 43, 358 (1978); J. Chem. Soc. Chem. Commun., 866 (1979); Tetrahedron Lett., Vol. 34, 8267 (1993); ibid., Vol. 33, 413 (1992).

If $R^1$ or $R^2$ comprises haloalkyl or haloalkenyl groups, the (S)-configuration is preferred for optically active amines of the formula VI.

The reaction mixtures are worked up conventionally, e.g. by mixing with water, separating the phases and possibly chromatographic purification of the crude products. Some of the intermediates and final products are obtained in the form of colorless or slightly brownish viscous oils which, under reduced pressure and at moderately elevated temperature, are freed or purified from volatile constituents. If the intermediates and final products are obtained as solids, the purification can also take place by recrystallization or trituration.

If individual compounds I are not accessible by the methods described above, they can be prepared by derivatization of other compounds I.

If isomeric mixtures are obtained in the synthesis, a separation is, however, generally not absolutely necessary, since the individual isomers can sometimes be converted into one another during preparation for application or upon application (e.g., under the effect of light, acid or bases). Corresponding conversions can also take place after application, for example, in the treatment of plants, in the treated plant or in the harmful fungus to be controlled.

Collective terms were used in the definitions of the symbols given in the above formulae, which collective terms are generally representative of the following substituents:

halogen: fluorine, chlorine, bromine and iodine;

alkyl: saturated, straight-chain or branched hydrocarbon radicals with 1 to 4, 6, 8 or 10 carbon atoms, e.g. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups with 1 to 10 carbon atoms (as mentioned above), in which the hydrogen atoms in these groups can be partially or completely replaced by halogen atoms as mentioned above, e.g. $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated, straight-chain or branched hydrocarbon radicals with 2 to 4, 6, 8 or 10 carbon atoms and a double bond in any position, e.g. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkadienyl: unsaturated, straight-chain or branched hydrocarbon radicals with 4, 6, 8 or 10 carbon atoms and two double bonds in any position;

haloalkenyl: unsaturated, straight-chain or branched hydrocarbon radicals with 2 to 10 carbon atoms and a double bond in any position (as mentioned above), in which the hydrogen atoms in these groups can be partially or completely replaced by halogen atoms as mentioned above, in particular fluorine, chlorine and bromine;

alkynyl: straight-chain or branched hydrocarbon groups with 2 to 4, 6, 8 or 10 carbon atoms and a triple bond in any position, e.g. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

haloalkynyl: unsaturated, straight-chain or branched hydrocarbon radicals with 2 to 8 carbon atoms and a triple bond in any position (as mentioned above), in which the hydrogen atoms in these groups can be partially or completely replaced by halogen atoms as mentioned above, in particular fluorine, chlorine and bromine;

cycloalkyl: saturated mono- or bicyclic hydrocarbon groups with 3 to 6 or 8 carbon ring members, e.g. $C_3$–$C_8$-cycloalkyl, such as cyclopropyl, cyclobutyl, cyclopentyl, cyclohexyl, cycloheptyl and cyclooctyl;

oxyalkylenoxy: unbranched divalent chains formed from 1 to 3 $CH_2$ groups in which both valencies are bonded to the backbone via an oxygen atom, e.g. $OCH_2O$, $OCH_2CH_2O$ and $OCH_2CH_2CH_2O$;

five- to ten-membered saturated, partially unsaturated or aromatic heterocycle containing one to four heteroatoms from the group consisting of O, N and S:
  5- or 6-membered heterocyclyl containing one to three nitrogen atoms and/or one oxygen or sulfur atom or one or two oxygen and/or sulfur atoms, e.g. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;

5-membered heteroaryl containing one to four nitrogen atoms or one to three nitrogen atoms and one sulfur or oxygen atom: 5-ring heteroaryl groups which, in addition to carbon atoms, can contain one to four nitrogen atoms or one to three nitrogen atoms and one sulfur or oxygen atom as ring members, e.g. 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl and 1,3,4-triazol-2-yl;

6-membered heteroaryl containing one to three or one to four nitrogen atoms: 6-ring heteroaryl groups which, in addition to carbon atoms, can contain one to three or one to four nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl;

alkylene: unbranched divalent chains formed from 3 to 5 $CH_2$ groups, e.g. $CH_2$, $CH_2CH_2$, $CH_2CH_2CH_2$, $CH_2CH_2CH_2CH_2$ and $CH_2CH_2CH_2CH_2CH_2$;

oxyalkylene: unbranched divalent chains formed from 2 to 4 $CH_2$ groups in which one valency is bonded to the backbone via an oxygen atom, e.g. $OCH_2CH_2$, $OCH_2CH_2CH_2$ and $OCH_2CH_2CH_2CH_2$;

oxyalkylenoxy: unbranched divalent chains formed from 1 to 3 $CH_2$ groups in which both valencies are bonded to the backbone via an oxygen atom, e.g. $OCH_2O$, $OCH_2CH_2O$ and $OCH_2CH_2CH_2O$.

The (R)- and (S)-isomers and the racemates of compounds of the formula I which have chiral centers are included in the present invention.

The embodiments of the intermediates which are especially preferred with regard to the variables correspond to those of the radicals $L^1$, $L^2$, $L^3$, $R^1$, $R^2$ and X of the formula I.

In view of the intended use of the triazolopyrimidines of the formula I, the following meanings of the substituents, in each case alone or in combination, are especially preferred:

Preference is given to compounds I in which $R^1$ is $C_1$–$C_3$-alkyl or $C_1$–$C_8$-haloalkyl.

Preference is similarly given to compounds I in which $R^1$ is a saturated or aromatic 5- or 6-membered heterocycle.

Preference is furthermore given to compounds I in which $R^1$ is $C_2$–$C_{10}$-alkenyl.

Compounds I are particularly preferred in which $R^1$ is a group B

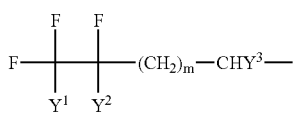

B in which
$Y^1$ represents hydrogen, fluorine or $C_1$–$C_6$-fluoroalkyl,
$Y^2$ represents hydrogen or fluorine, or $Y^1$ and $Y^2$ together form a double bond;
m represents 0 or 1; and
$Y^3$ represents hydrogen or methyl.

Preference is furthermore given to compounds I in which $R^1$ is $C_3$–$C_6$-cycloalkyl which can be substituted by $C_1$–$C_4$-alkyl.

Preference is particularly given to compounds I in which $R^2$ represents hydrogen.

Similarly preferred are compounds I in which $R^2$ is methyl or ethyl.

If $R^1$ and/or $R^2$ comprise haloalkyl or haloalkenyl groups with a center of chirality, the (S)-isomers are preferred.

Furthermore, particular preference is given to compounds I in which $R^1$ and $R^2$, together with the nitrogen atom to which they are bonded, form a five- or six-membered ring which can be interrupted by an atom from the group consisting of O, N and S and/or can carry one or more substituents from the group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1$–$C_4$-alkylene chain.

Particular preference is especially given to compounds I in which $R^1$ and $R^2$, together with the nitrogen atom to which they are bonded, form a piperidinyl ring which is optionally substituted by one to three halogen, $C_1$–$C_4$-alkyl or $C_1$–$C_4$-haloalkyl groups, in particular by a 4-methyl group.

Particular preference is furthermore given to compounds I in which $L^1$ represents methyl or ethyl, in particular methyl.

Similarly particularly preferred are compounds I in which $L^3$ represents halogen.

Particular preference is given to compounds I in which X represents halogen or $C_1$–$C_4$-alkyl, such as chlorine or methyl, in particular chlorine.

Particular preference is given, in view of their use, to the compounds I compiled in the following tables. The groups mentioned in the tables for a substituent additionally represent, considered per se, independently of the combination in which they are mentioned, a particularly preferred embodiment of the substituent in question.

Table 1
Compounds of the formula I in which X is chlorine, $L^1$ is methyl, $L^2$ is fluorine and $L^3$ is hydrogen and the combination of $R^1$ and $R^2$ for a compound each time corresponds to a row of table A Table 2
Compounds of the formula I in which X is chlorine, $L^1$ is methyl and $L^2$ and $L^3$ are fluorine and the combination of $R^1$ and $R^2$ for a compound each time corresponds to a row of table A Table 3
Compounds of the formula I in which X is chlorine, $L^1$ is methyl, $L^2$ is chlorine and $L^3$ is hydrogen and the combination of $R^1$ and $R^2$ for a compound each time corresponds to a row of table A Table 4
Compounds of the formula I in which X is chlorine, $L^1$ is methyl and $L^2$ and $L^3$ are chlorine and the combination of $R^1$ and $R^2$ for a compound each time corresponds to a row of table A Table 5
Compounds of the formula I in which X is chlorine, $L^1$ is ethyl, $L^2$ is fluorine and $L^3$ is hydrogen and the combination of $R^1$ and $R^2$ for a compound each time corresponds to a row of table A Table 6
Compounds of the formula I in which X is chlorine, $L^1$ is ethyl and $L^2$ and $L^3$ are fluorine and the combination of $R^1$ and $R^2$ for a compound each time corresponds to a row of table A Table 7
Compounds of the formula I in which X is chlorine, $L^1$ is ethyl, $L^2$ is chlorine and $L^3$ is hydrogen and the combination of $R^1$ and $R^2$ for a compound each time corresponds to a row of table A Table 8
Compounds of the formula I in which X is chlorine, $L^1$ is ethyl and $L^2$ and $L^3$ are chlorine and the combination of $R^1$ and $R^2$ for a compound each time corresponds to a row of table A Table 9
Compounds of the formula I in which X is cyano, $L^1$ is methyl, $L^2$ is fluorine and $L^3$ is hydrogen and the combination of $R^1$ and $R^2$ for a compound each time corresponds to a row of table A Table 10
Compounds of the formula I in which X is cyano, $L^1$ is methyl and $L^2$ and $L^3$ are fluorine and the combination of $R^1$ and $R^2$ for a compound each time corresponds to a row of table A Table 11
Compounds of the formula I in which X is cyano, $L^1$ is methyl, $L^2$ is chlorine and $L^3$ is hydrogen and the combination of $R^1$ and $R^2$ for a compound each time corresponds to a row of table A Table 12
Compounds of the formula I in which X is cyano, $L^1$ is methyl and $L^2$ and $L^3$ are chlorine and the combination of $R^1$ and $R^2$ for a compound each time corresponds to a row of table A Table 13
Compounds of the formula I in which X is cyano, $L^1$ is ethyl, $L^2$ is fluorine and $L^3$ is hydrogen and the combination of $R^1$ and $R^2$ for a compound each time corresponds to a row of table A Table 14
Compounds of the formula I in which X is cyano, $L^1$ is ethyl and $L^2$ and $L^3$ are fluorine and the combination of $R^1$ and $R^2$ for a compound each time corresponds to a row of table A Table 15
Compounds of the formula I in which X is cyano, $L^1$ is ethyl, $L^2$ is chlorine and $L^3$ is hydrogen and the combination of $R^1$ and $R^2$ for a compound each time corresponds to a row of table A Table 16
Compounds of the formula I in which X is cyano, $L^1$ is ethyl and $L^2$ and $L^3$ are chlorine and the combination of $R^1$ and $R^2$ for a compound each time corresponds to a row of table A Table 17
Compounds of the formula I in which X and $L^1$ are methyl, $L^2$ is fluorine and $L^3$ is hydrogen and the combination of $R^1$ and $R^2$ for a compound each time corresponds to a row of table A Table 18
Compounds of the formula I in which X and $L^1$ are methyl and $L^2$ and $L^3$ are fluorine and the combination of $R^1$ and $R^2$ for a compound each time corresponds to a row of table A Table 19
Compounds of the formula I in which X and $L^1$ are methyl, $L^2$ is chlorine and $L^3$ is hydrogen and the combination of $R^1$ and $R^2$ for a compound each time corresponds to a row of table A Table 20
Compounds of the formula I in which X and $L^1$ are methyl and $L^2$ and $L^3$ are chlorine and the combination of $R^1$ and $R^2$ for a compound each time corresponds to a row of table A Table 21
Compounds of the formula I in which X is methyl, $L^1$ is ethyl, $L^2$ is fluorine and $L^3$ is hydrogen and the combination of $R^1$ and $R^2$ for a compound each time corresponds to a row of table A Table 22
Compounds of the formula I in which X is methyl, $L^1$ is ethyl and $L^2$ and $L^3$ are fluorine and the combination of $R^1$ and $R^2$ for a compound each time corresponds to a row of table A Table 23
Compounds of the formula I in which X is methyl, $L^1$ is ethyl, $L^2$ is chlorine and $L^3$ is hydrogen and the combination of $R^1$ and $R^2$ for a compound each time corresponds to a row of table A Table 24
Compounds of the formula I in which X is methyl, $L^1$ is ethyl and $L^2$ and $L^3$ are chlorine and the combination of $R^1$ and $R^2$ for a compound each time corresponds to a row of table A Table 25
Compounds of the formula I in which X is methoxy, $L^1$ is methyl, $L^2$ is fluorine and $L^3$ is hydrogen and the combination of $R^1$ and $R^2$ for a compound each time corresponds to a row of table A Table 26
Compounds of the formula I in which X is methoxy, $L^1$ is methyl and $L^2$ and $L^3$ are fluorine and the combination of $R^1$ and $R^2$ for a compound each time corresponds to a row of table A Table 27
Compounds of the formula I in which X is methoxy, $L^1$ is methyl, $L^2$ is chlorine and $L^3$ is hydrogen and the combination of $R^1$ and $R^2$ for a compound each time corresponds to a row of table A Table 28
Compounds of the formula I in which X is methoxy, $L^1$ is methyl and $L^2$ and $L^3$ are chlorine and the combination of $R^1$ and $R^2$ for a compound each time corresponds to a row of table A Table 29

Compounds of the formula I in which X is methoxy, $L^1$ is ethyl, $L^2$ is fluorine and $L^3$ is hydrogen and the combination of $R^1$ and $R^2$ for a compound each time corresponds to a row of table A Table 30

Compounds of the formula I in which X is methoxy, $L^1$ is ethyl and $L^2$ and $L^3$ are fluorine and the combination of $R^1$ and $R^2$ for a compound each time corresponds to a row of table A Table 31

Compounds of the formula I in which X is methoxy, $L^1$ is ethyl, $L^2$ is chlorine and $L^3$ is hydrogen and the combination of $R^1$ and $R^2$ for a compound each time corresponds to a row of table A Table 32

Compounds of the formula I in which X is methoxy, $L^1$ is ethyl and $L^2$ and $L^3$ are chlorine and the combination of $R^1$ and $R^2$ for a compound each time corresponds to a row of table A

TABLE A

| No. | $R^1$ | $R^2$ |
|---|---|---|
| A-1 | H | H |
| A-2 | $CH_2CH_3$ | H |
| A-3 | $CH_2CH_3$ | $CH_3$ |
| A-4 | $CH_2CH_3$ | $CH_2CH_3$ |
| A-5 | $CH_2CF_3$ | H |
| A-6 | $CH_2CF_3$ | $CH_3$ |
| A-7 | $CH_2CF_3$ | $CH_2CH_3$ |
| A-8 | $CH_2CCl_3$ | H |
| A-9 | $CH_2CCl_3$ | $CH_3$ |
| A-10 | $CH_2CCl_3$ | $CH_2CH_3$ |
| A-11 | $CH_2CH_2CH_3$ | H |
| A-12 | $CH_2CH_2CH_3$ | $CH_3$ |
| A-13 | $CH_2CH_2CH_3$ | $CH_2CH_3$ |
| A-14 | $CH_2CH_2CH_3$ | $CH_2CH_2CH_3$ |
| A-15 | $CH(CH_3)_2$ | H |
| A-16 | $CH(CH_3)_2$ | $CH_3$ |
| A-17 | $CH(CH_3)_2$ | $CH_2CH_3$ |
| A-18 | $(\pm)CH(CH_3)$—$CF_3$ | H |
| A-19 | $(\pm)CH(CH_3)$—$CF_3$ | $CH_3$ |
| A-20 | $(\pm)CH(CH_3)$—$CF_3$ | $CH_2CH_3$ |
| A-21 | $(S)CH(CH_3)$—$CF_3$ | H |
| A-22 | $(S)CH(CH_3)$—$CF_3$ | $CH_3$ |
| A-23 | $(S)CH(CH_3)$—$CF_3$ | $CH_2CH_3$ |
| A-24 | $(R)CH(CH_3)$—$CF_3$ | H |
| A-25 | $(R)CH(CH_3)$—$CF_3$ | $CH_3$ |
| A-26 | $(R)CH(CH_3)$—$CF_3$ | $CH_2CH_3$ |
| A-27 | $(\pm)CH(CH_3)$—$CCl_3$ | H |
| A-28 | $(\pm)CH(CH_3)$—$CCl_3$ | $CH_3$ |
| A-29 | $(\pm)CH(CH_3)$—$CCl_3$ | $CH_2CH_3$ |
| A-30 | $(S)CH(CH_3)$—$CCl_3$ | H |
| A-31 | $(S)CH(CH_3)$—$CCl_3$ | $CH_3$ |
| A-32 | $(S)CH(CH_3)$—$CCl_3$ | $CH_2CH_3$ |
| A-33 | $(R)CH(CH_3)$—$CCl_3$ | H |
| A-34 | $(R)CH(CH_3)$—$CCl_3$ | $CH_3$ |
| A-35 | $(R)CH(CH_3)$—$CCl_3$ | $CH_2CH_3$ |
| A-36 | $CH_2CF_2CF_3$ | H |
| A-37 | $CH_2CF_2CF_3$ | $CH_3$ |
| A-38 | $CH_2CF_2CF_3$ | $CH_2CH_3$ |
| A-39 | $CH_2(CF_2)_2CF_3$ | H |
| A-40 | $CH_2(CF_2)_2CF_3$ | $CH_3$ |
| A-41 | $CH_2(CF_2)_2CF_3$ | $CH_2CH_3$ |
| A-42 | $CH_2C(CH_3)$=$CH_2$ | H |
| A-43 | $CH_2C(CH_3)$=$CH_2$ | $CH_3$ |
| A-44 | $CH_2C(CH_3)$=$CH_2$ | $CH_2CH_3$ |
| A-45 | cyclopentyl | H |
| A-46 | cyclopentyl | $CH_3$ |
| A-47 | cyclopentyl | $CH_2CH_3$ |
| A-48 | cyclohexyl | H |
| A-49 | cyclohexyl | $CH_3$ |
| A-50 | cyclohexyl | $CH_2CH_3$ |
| A-51 | | —$(CH_2)_2CH$=$CHCH_2$— |
| A-52 | | —$(CH_2)_2C(CH_3)$=$CHCH_2$— |
| A-53 | | —$(CH_2)_2CH(CH_3)(CH_2)_2$— |
| A-54 | | —$(CH_2)_2CHF(CH_2)_2$— |
| A-55 | | —$(CH_2)_3CHFCH_2$— |
| A-56 | | —$(CH_2)_2CH(CF_3)(CH_2)_2$— |
| A-57 | | —$(CH_2)_2O(CH_2)_2$— |
| A-58 | | —$(CH_2)_2S(CH_2)_2$— |
| A-59 | | —$(CH_2)_5$— |
| A-60 | | —$(CH_2)_4$— |
| A-61 | | —$CH_2CH$=$CHCH_2$— |
| A-62 | | —$CH(CH_3)(CH_2)_3$— |
| A-63 | | —$CH_2CH(CH_3)(CH_2)_2$— |

The compounds I are suitable as fungicides. They are distinguished by an outstanding effectiveness against a broad spectrum of phytopathogenic fungi, especially from the classes of the *Ascomycetes*, *Deuteromycetes*, *Phycomycetes* and *Basidiomycetes*. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soy, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,

*Botrytis cinerea* (gray mold) on strawberries, vegetables, ornamental plants and grapevines,

*Cercospora arachidicola* on peanuts,

*Erysiphe cichoracearum* and *Sphaerotheca fuliginea* on cucurbits,

*Blumeria graminis* (powdery mildew) on cereals,

*Fusarium* and *Verticillium* species on various plants,

*Helminthosporium* species on cereals,

*Mycosphaerella* species on bananas and peanuts,

*Phytophthora infestans* on potatoes and tomatoes,

*Plasmopara viticola* on grapevines,

*Podosphaera leucotricha* on apples,

*Pseudocercosporella herpotrichoides* on wheat and barley,

*Pseudoperonospora* species on hops and cucumbers,

*Puccinia* species on cereals,

*Pyricularia oryzae* on rice,

*Rhizoctonia* species on cotton, rice and lawns,

*Septoria nodorum* on wheat,

*Uncinula necator* on grapevines,

*Ustilago* species on cereals and sugar cane, and

*Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the effect desired. Amounts customarily applied in the protection of materials are, for example, 0.001 g to 2 kg, preferably 0.005 g to 1 kg, of active compound per cubic meter of treated material.

The compounds I can be converted to the usual formulations, e.g. solutions, emulsions, suspensions, dusts, powders, pastes and granules. The application form depends on the respective use intended; it should in any case guarantee a fine and uniform distribution of the compound according to the invention.

The formulations are prepared in a known way, e.g. by extending the active compound with solvents and/or carriers, if desired using emulsifiers and dispersants, it being possible, when water is the diluent, also to use other organic solvents as auxiliary solvents. Suitable auxiliaries for this purpose are essentially: solvents, such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic ores (e.g. highly dispersed silicic acid, silicates); emulsifiers, such as nonionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are alkali metal, alkaline earth metal and ammonium salts of lignosulfonic acid, naphthalenesulfonic acid, phenolsulfonic acid and dibutylnaphthalenesulfonic acid, alkylarylsulfonates, alkyl sulfates, alkylsulfonates, fatty alcohol sulfates and fatty acids, and alkali metal and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Petroleum fractions having medium to high boiling points, such as kerosene or diesel fuel, furthermore coal tar oils, and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, or highly polar solvents, e.g. dimethylformamide, dimethyl sulfoxide, N-methylpyrrolidone or water, are suitable for the preparation of directly sprayable solutions, emulsions, pastes or oil dispersions.

Powders, combinations for broadcasting and dusts can be prepared by mixing or mutually grinding the active substances with a solid carrier.

Granules, e.g. coated granules, impregnated granules and homogeneous granules, can be prepared by binding the active compounds to solid carriers. Solid carriers are, e.g., mineral earths, such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate or ureas, and plant products, such as cereal meal, tree bark meal, wood meal and nutshell meal, cellulose powders and other solid carriers.

The formulations generally comprise between 0.01 and 95% by weight, preferably between 0.1 and 90% by weight, of the active compound. The active compounds are employed therein in a purity of 90% to 100%, preferably 95% to 100% (according to the NMR spectrum).

Examples for Formulations are:

I. 5 parts by weight of a compound according to the invention are intimately mixed with 95 parts by weight of finely divided kaolin. In this way, a dust comprising 5% by weight of the active compound is obtained.

II. 30 parts by weight of a compound according to the invention are intimately mixed with a mixture of 92 parts by weight of pulverulent silica gel and 8 parts by weight of liquid paraffin, which had been sprayed onto the surface of this silica gel. In this way, an active compound preparation with good adhesive properties (active compound content 23% by weight) is obtained.

III. 10 parts by weight of a compound according to the invention are dissolved in a mixture consisting of 90 parts by weight of xylene, 6 parts by weight of the addition product of 8 to 10 mol of ethylene oxide with 1 mol of the N-monoethanolamide of oleic acid, 2 parts by weight of the calcium salt of dodecylbenzenesulfonic acid and 2 parts by weight of the addition product of 40 mol of ethylene oxide with 1 mol of castor oil (active compound content 9% by weight).

IV. 20 parts by weight of a compound according to the invention are dissolved in a mixture consisting of 60 parts by weight of cyclohexanone, 30 parts by weight of isobutanol, 5 parts by weight of the addition product of 7 mol of ethylene oxide with 1 mol of isooctylphenol and 5 parts by weight of the addition product of 40 mol of ethylene oxide with 1 mol of castor oil (active compound content 16% by weight).

V. 80 parts by weight of a compound according to the invention are intimately mixed with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel and are ground in a hammer mill (active compound content 80% by weight).

VI. 90 parts by weight of a compound according to the invention are mixed with 10 parts by weight of N-methyl-α-pyrrolidone and a solution is obtained which is suitable for use in the form of very small drops (active compound content 90% by weight).

VII. 20 parts by weight of a compound according to the invention are dissolved in a mixture consisting of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. By running the solution into 100000 parts by weight of water and finely dispersing it therein, an aqueous dispersion is obtained comprising 0.02% by weight of the active compound.

VIII. 20 parts by weight of a compound according to the invention are intimately mixed with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel and are ground in a hammer mill. A spray emulsion comprising 0.1% by weight of the active compound is obtained by fine dispersion of the mixture in 20000 parts by weight of water.

The active compounds can be used as such, in the form of their formulations or of the application forms prepared therefrom, e.g. in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; they should in any case guarantee the finest possible dispersion of the active compounds according to the invention.

Aqueous application forms can be prepared from emulsion concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, concentrates comprising active substance, wetting agent, tackifier, dispersant or emulsifier and possibly solvent or oil can also be prepared, which concentrates are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra low volume (ULV) process, it being possible to apply formulations with more than 95% by weight of active compound or even the active compound without additives.

Oils of various types, herbicides, fungicides, other pesticides and bactericides can be added to the active compounds, if need be also not until immediately before use (tank mix). These agents can be added to the compositions according to the invention in a weight ratio of 1:10 to 10:1.

The compositions according to the invention can, in the application form as fungicides, also be present together with other active compounds, e.g. with herbicides, insecticides, growth regulators, fungicides or also with fertilizers. On mixing the compounds I or the compositions comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N'-ethylenebisdithiocarbamate), ammonia complex of zinc (N,N'-propylenebisdithiocarbamate), zinc (N,N'-propylenebisdithiocarbamate) or N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate or diisopropyl 5-nitroisophthalate;

heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-(methoxycarbonylamino)benzimidazole, 2-(2-furyl)benzimidazole, 2-(4-thiazolyl)benzimidazole, N-(1,1,2,2-tetrachloroethylthio)tetrahydrophthalimide, N-(trichloromethylthio)tetrahydrophthalimide or N-(trichloromethylthio)phthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazin-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-(tert-butyl)phenyl)-2-methylpropyl]-cis-2,6-dimethylmorpholine, N-[3-(p-(tert-butyl)phenyl)-2-methyl propyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-(n-propyl)-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene or 1,2-bis(3-methoxycarbonyl-2-thioureido)benzene, strobilurins, such as methyl E-methoxyimino[α-(o-tolyloxy)-o-tolyl]acetate, methyl E-2-{2-[6-(2-cyanophenoxy)pyrimidin-4-yloxy]phenyl}-3-methoxyacrylate, methyl E-methoxyimino[α-(2-phenoxyphenyl)]acetamide, methyl E-methoxyimino[α-(2,5-dimethylphenoxy)-o-tolyl]acetamide, methyl E-2-{2-[[2-trifluoromethylpyrid-6-yl]oxymethyl]phenyl}-3-methoxyacrylate, methyl (E,E)-methoxy-imino{2-[1-(3-trifluoromethylphenyl)ethylideneaminooxymethyl]- phenyl}acetate or methyl N-(2-{[1-(4-chlorophenyl)-1H-pyrazol-3-yl]oxymethyl}phenyl)-N-methoxycarbamate, anilinopyrimidines, such as N-(4,6-dimethylpyrimidin-2-yl)aniline, N-[4-methyl-6-(1-propynyl)pyrimidin-2-yl]aniline or N-[4-methyl-6-cyclopropylpyrimidin-2-yl]aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)acryloylmorpholine or 3-(4-fluorophenyl-3-(3,4-dimethoxyphenyl)acryloylmorpholine, and various fungicides, such as dodecylguanidine acetate, 1-(3-bromo-6-methoxy-2-methylphenyl)-1-(2,3,4-trimethoxy-6-methylphenyl)methanone, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, N-(2,6-dimethylphenyl)-N-(2'-methoxyacetyl)-DL-alanine methyl ester, N-(2,6-dimethylphenyl)-N-chloroacetyl-D,L-2-aminobutyrolactone, N-(2,6-dimethylphenyl)-N-(phenylacetyl)-DL-alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoxyimino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, 5-chloro-2-cyano-4-(p-tolyl)imidazole-1-sulfonic acid dimethylamide or 3,5-dichloro-N-(3-chloro-1-ethyl-1-methyl-2-oxopropyl)-4-methylbenzamide.

SYNTHESIS EXAMPLES

The procedures described in the following synthesis examples were used to prepare further compounds I by appropriate modification of the starting compounds. The compounds thus obtained are listed in the following table, together with physical data.

Example 1

Preparation of diethyl (2-fluoro-4-methylphenyl)malonate 0.49 mol of diethyl malonate was added at 60° C. inside 2 hours to a mixture of 0.51 mol of NaH and 140 ml of 1,4-dioxane. The mixture was stirred for approximately 10 min at 60° C. and then 0.05 mol of Cu(I)Br was added. After 15 min, a mixture of 0.25 mol of 4-bromo-3-fluorotoluene and 10 ml of 1,4-dioxane was added. The reaction mixture was heated at 100° C. for approximately 15 hours and was then cooled to 15° C. After acidifying with 35 ml of 12N HCl at 15 to 20° C., the precipitate produced was filtered off. The filtrate was extracted and the organic phases, after separation, were dried and then freed from the solvent. 40 g of the title compound were obtained.

Example 2

Preparation of 5,7-dihydroxy-6-(2-fluoro-4-methylphenyl)-[1,2,4]triazolo[1,5-a]pyrimidine A mixture of 14 g of 3-amino-1,2,4-triazole, 0.17 mol of malonate from Ex. 1 and 50 ml of tributylamine were heated at 180° C. for 6 hours and then cooled to 70° C. After addition of a solution of 21 g of NaOH in 200 ml of water, the mixture was stirred for a further 30 min, then the organic phase was separated and the aqueous phase was extracted with diethyl ether. The product was precipitated from the aqueous phase by acidification with conc. HCl. The precipitate was filtered off and dried. 39 g of the title compound were obtained.

Example 3

Preparation of 5,7-dichloro-6-(2-fluoro-4-methylphenyl)-[1,2,4]triazolo[1,5-a]pyrimidine A mixture of 30 g of the compound from Ex. 2 and 50 ml of $POCl_3$ was refluxed for 8 hours, a portion of the $POCl_3$ being distilled off. The residue was added to a mixture of $CH_2Cl_2$ and water and the organic phase was separated, dried and freed from the solvent. 26 g of the title compound with a melting point of 152° C. were obtained from the residue.

Example 4

Preparation of 5-chloro-6-(2-fluoro-4-methylphenyl)-7-isopropylamino-[1,2,4]triazolo[1,5-a]pyrimidine [I-2]

A solution of 1.5 mmol of isopropylamine and 1.5 mmol of triethylamine in 10 ml of $CH_2Cl_2$ was added with stirring to a solution of 1.5 mmol of the compound from Ex. 3 in 20 ml of $CH_2Cl_2$. The reaction mixture was stirred at 20 to 25° C. for 16 hours and was then washed with dilute HCl. The organic phase was separated, dried and freed from the solvent. After chromatography on silica gel, 420 mg of the title compound with a melting point of 121° C. were obtained from the residue.

Example 5

Preparation of 5-cyano-6-(2-fluoro-4-methylphenyl)-7-(4-methylpiperidin-1-yl)-[1,2,4]triazolo[1,5-a]pyrimidine A mixture of 0.1 mol of compound I-3 and 0.25 mol of $N(C_2H_5)_4CN$ in 750 ml of dimethylformamide (DMF) was stirred at 20–25° C. for approximately 16 hours. After mixing with water and methyl tert-butyl ether (MTBE), the organic phase was separated, washed with water and, after drying, freed from the solvent. After chromatography on silica gel, 6.23 g of the title compound were obtained from the residue.

$^1$H-NMR: 8.5 (s); 7.3 (t); 7.2 (d); 7.05 (d); 3.95 (d); 3.65 (d); 2.8 (t); 2.8 (t); 2.5 (s); 1.6 (m); 1.5 (m); 1.3 (m); 1.0 (d).

Example 6

Preparation of 5-methoxy-6-(2-fluoro-4-methylphenyl)-7-(4-methylpiperidin-1-yl)-[1,2,4]triazolo[1,5-a]pyrimidine A 30% by weight solution of 71.5 mmol of NaOCH$_3$ was mixed with a solution of 65 mmol of compound I-3 in 400 ml of anhydrous ethanol. After stirring at 20–25° C. for approximately 16 hours, ethanol was distilled off and the residue was taken up in CH$_2$Cl$_2$. The organic phase was washed with water and, after drying, freed from the solvent. After chromatography on silica gel, 3.98 g of the title compound with a melting point of 201° C. were obtained from the residue.

20 hours. 50 ml of an aqueous NH$_4$Cl solution were added and then acidification was carried out with dilute HCl solution. After extraction with MTBE and phase separation, the organic phases were dried and evaporated. The residue was purified by chromatography on silica gel. The eluate was taken up in concentrated HCl solution and held at 80° C. for 24 hours. After cooling, the solution was adjusted to pH 5 with aqueous NaOH solution. After extraction with MTBE and phase separation, the organic phases were dried and freed from the solvent. After chromatography on silica gel, 0.72 g of the title compound was obtained from the residue.

$^1$H-NMR: 8.3 (s); 7.05 (m); 3.75 (d); 3.45 (d); 2.7 (t); 2.7 (t); 2.5 (s); 2.35 (s); 1.6 (m); 1.5 (m); 1.3 (m); 0.9 (d).

TABLE I

Compounds of the formula I:

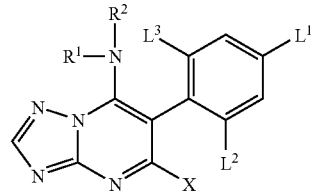

I

| No. | R$^1$ | R$^2$ | L$^1$ | L$^2$ | L$^3$ | X | Phys. data (M.p.[° C.]) |
|---|---|---|---|---|---|---|---|
| I-1 | CH$_2$C(CH$_3$)=CH$_2$ | CH$_2$CH$_3$ | CH$_3$ | F | H | Cl | 105 |
| I-2 | CH(CH$_3$)$_2$ | H | CH$_3$ | F | H | Cl | 121 |
| I-3 | —(CH$_2$)$_2$CH(CH$_3$)(CH$_2$)$_2$— | | CH$_3$ | F | H | Cl | 151 |
| I-4 | Cyclopentyl | H | CH$_3$ | F | H | Cl | 145 |
| I-5 | CH$_2$CH$_3$ | CH$_2$CH$_3$ | CH$_3$ | F | H | Cl | 127 |
| I-6 | CH$_2$CH$_2$CH$_3$ | CH$_2$CH$_2$CH$_3$ | CH$_3$ | F | H | Cl | 97 |
| I-7 | CH(CH$_3$)$_2$ | CH$_3$ | CH$_3$ | F | H | Cl | 188 |
| I-8 | (±) CH(CH$_3$)—CF$_3$ | H | CH$_3$ | F | H | Cl | A) 147; B) 139 |
| I-9 | (S) CH(CH$_3$)—CF$_3$ | H | CH$_3$ | F | H | Cl | A) 155; B) 154 |
| I-10 | (R) CH(CH$_3$)—CF$_3$ | H | CH$_3$ | F | H | Cl | A) 155; B) 154 |
| I-11 | CH$_2$CF$_3$ | H | CH$_3$ | F | H | Cl | 127 |
| I-12 | CH$_2$CF$_2$CF$_3$ | H | CH$_3$ | F | H | Cl | 187 |
| I-13 | CH$_2$CF$_2$CF$_2$CF$_3$ | H | CH$_3$ | F | H | Cl | 124 |
| I-14 | H | H | CH$_3$ | F | H | Cl | 247 |
| I-15 | —(CH$_2$)$_2$CH(CH$_3$)(CH$_2$)$_2$— | | CH$_3$ | F | H | CN | (see Ex. 5) |
| I-16 | —(CH$_2$)$_2$CH(CH$_3$)(CH$_2$)$_2$— | | CH$_3$ | F | H | OCH$_3$ | (see Ex. 6) |
| I-17 | —(CH$_2$)$_2$CH(CH$_3$)(CH$_2$)$_2$— | | CH$_3$ | F | H | CH$_3$ | (see Ex. 7) |
| I-18 | CH$_2$C(CH$_3$)=CH$_2$ | CH$_2$CH$_3$ | CH$_3$ | F | F | Cl | 123 |
| I-19 | —(CH$_2$)$_2$CH(CH$_3$)(CH$_2$)$_2$— | | CH$_3$ | F | F | Cl | 140 |
| I-20 | (±) CH(CH$_3$)—CF$_3$ | H | CH$_3$ | F | F | Cl | 154 |
| I-21 | (S) CH(CH$_3$)—CF$_3$ | H | CH$_3$ | F | F | Cl | 163 |
| I-22 | (R) CH(CH$_3$)—CF$_3$ | H | CH$_3$ | F | F | Cl | 163 |
| I-23 | CH$_2$CF$_3$ | H | CH$_3$ | F | F | Cl | 168 |

In the case of chiral R$^1$ groups, two diastereoisomers A) and B) may exist because of the hindered rotation of the phenyl group, which diastereoisomers may differ in their physical properties.

Example 7

Preparation of 5-methyl-6-(2-fluoro-4-methylphenyl)-7-(4-methylpiperidin-1-yl)-[1,2,4]triazolo[1,5-a]pyrimidine A mixture of 20 ml of diethyl malonate and 0.27 g (5.65 mmol) of a 50% by weight dispersion of NaH in mineral oil in 50 ml of acetonitrile was stirred at 20–25° C. for approximately two hours. 4.71 mmol of compound I-3 were added and then the mixture was stirred at 60° C. for approximately

Examples for the Action Against Harmful Fungi

The fungicidal action of the compounds of the general formula I can be demonstrated from the following tests:

The active compounds were prepared, separately or together, as a 10% emulsion in a mixture of 70% by weight of cyclohexanone, 20% by weight of Nekanil® LN (Lutensol® AP6, wetting agent with an emulsifying and dispersing action based on ethoxylated alkylphenols) and 10% by weight of Wettol® EM (nonionic emulsifier based on ethoxylated castor oil) and were appropriately diluted with water to the desired concentration.

Use Example 1

Activity Against Early Blight of Tomato Caused by Alternaria solani

Leaves of pot plants of the variety "Große Fleischtomate St. Pierre" were sprayed to runoff point with an aqueous suspension prepared from a stock solution consisting of 10% of active compound, 85% of cyclohexanone and 5% of emulsifier. On the following day, the leaves were infected with an aqueous suspension of zoospores of Alternaria solani in 2% Biomalz solution with a concentration of $0.17 \times 10^6$ spores/ml. The plants were subsequently placed in a chamber saturated with water vapor at temperatures between 20 and 22° C. After 5 days, early blight in the untreated but infected control plants had so extensively developed that the infection could be visually determined in %.

In this test, the plants treated with 250 ppm of the active compounds Nos. I-1 to I-4, I-8A, I-8B, I-11 and I-17 of table I showed not more than 3% infection, while the untreated plants were 90% infected.

Use Example 2

Activity Against Net Blotch of Barley Caused by Pyrenophora teres

Leaves of pot-grown barley seedlings of the variety "Igri" were sprayed to runoff point with an aqueous preparation of active compound prepared from a stock solution consisting of 10% of active compound, 85% of cyclohexanone and 5% of emulsifier. 24 hours after the spray coating had dried on, the leaves were inoculated with an aqueous suspension of spores of Pyrenophora [syn. Drechslera] teres, the causative agent of net blotch. The test plants were subsequently placed in a greenhouse at temperatures of between 20 and 24° C. and a relative atmospheric humidity of 95 to 100%. After 6 days, the extent of development of the disease was determined visually in % of infection of the total leaf area.

In this test, the plants treated with 250 ppm of the active compounds Nos. I-2 to I-4, I-8B and I-11 of table I showed no to a maximum of 7% infection, while the untreated plants were 100% infected.

Use Example 3

Protective Activity Against Rice Blast Disease Caused by Pyricularia oryzae

Leaves of pot-grown rice seedlings of the variety "Tai-Nong 67" were sprayed to run off point with an aqueous preparation of active compound prepared from a stock solution consisting of 10% of active compound, 85% of cyclohexanone and 5% of emulsifier. On the following day, the plants were inoculated with an aqueous suspension of spores of Pyricularia oryzae. The experimental plants were subsequently placed in a climatic chamber at 22–24° C. and 95–99% relative humidity for 6 days. The extent of the development of infection on the leaves was then determined visually.

In this test, the plants treated with 250 ppm of the active compounds Nos. I-1, I-3, I-4, I-8A, I-8B, I-11 and I-17 of table I showed no more than 15% infection, while the untreated plants were 80% infected.

We claim:
1. A triazolopyrimidine of the formula I

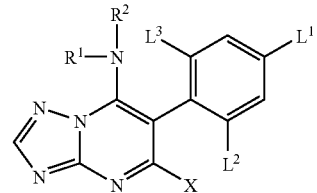

in which the substituents have the following meanings:
$L^1$ is $C_1$–$C_4$-alkyl;
$L^2$ is halogen;
$L^3$ is hydrogen or halogen;
X is halogen, cyano, $C_1$–$C_4$-alkyl, $C_1$–$C_4$-alkoxy or $C_1$–$C_2$-haloalkoxy;
$R^1$, $R^2$ are, independently of one another, hydrogen, $C_1$–$C_3$-alkyl, $C_1$–$C_{10}$-haloalkyl, $C_3$–$C_8$-cycloalkyl, $C_2$–$C_{10}$-alkenyl, $C_4$–$C_{10}$-alkadienyl, $C_2$–$C_{10}$-alkynyl or $C_4$–$C_{10}$-alkyl, which has no center of chirality, or $C_3$–$C_6$-cycloalkynyl, phenyl, naphthyl, or a five- to ten-membered saturated, partially unsaturated or aromatic heterocycle, containing one to four heteroatoms from the group consisting of O, N and S,
$R^1$ and $R^2$ can also, together with the nitrogen atom to which they are bonded, form a five- or six-membered ring which can be interrupted by an atom from the group consisting of O, N and S and/or can carry one or more substituents from the group consisting of halogen, $C_1$–$C_6$-alkyl, $C_f$–$C_6$-haloalkyl and oxy-$C_1$–$C_3$-alkylenoxy or in which an N and a neighboring C atom can be connected via a $C_1$–$C_4$-alkylene chain;
wherein $R^1$ and/or $R^2$ can be substituted by one to three identical or different groups $R^a$:
$R^a$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di($C_1$–$C_6$-alkyl)amino, $C_2$–$C_6$-alkenyl, $C_2$–$C_6$-alkenyloxy, $C_3$–$C_6$-alkynyloxy, $C_3$–$C_6$-cycloalkyl, phenyl, naphthyl or a five- to ten-membered saturated, partially unsaturated or aromatic heterocycle, containing one to four heteroatoms from the group consisting of O, N and S,
wherein these aliphatic, alicyclic or aromatic groups, for their part, can be partially or completely halogenated or can carry one to three groups $R^b$:
$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl or dialkylaminothiocarbonyl, wherein the alkyl groups in these radicals contain 1 to 6 carbon atoms and the alkenyl or alkynyl groups mentioned in these radicals contain 2 to 8 carbon atoms;
and/or one to three of the following radicals:
cycloalkyl, cycloalkoxy, heterocyclyl or heterocyclyloxy, wherein the cyclic systems contain 3 to 10 ring members; aryl, aryloxy, arylthio, aryl-$C_1$–$C_6$-alkoxy, aryl-$C_1$–$C_6$-alkyl, hetaryl, hetaryloxy or hetarylthio, wherein the aryl radicals preferably contain 6 to 10 ring members and the hetaryl radicals contain 5 or 6 ring members, wherein the cyclic systems can be partially or completely halogenated or can be substituted by alkyl or haloalkyl groups.

2. A compound of the formula I as claimed in claim 1, in which $R^1$ and $R^2$ have the following meanings:

$R^1$, $R^2$ are, independently of one another, hydrogen, $C_1$–$C_3$-alkyl, $C_1$–$C_{10}$-haloalkyl, $C_3$–$C_8$-cycloalkyl, $C_2$–$C_{10}$-alkenyl, $C_4$–$C_{10}$-alkadienyl, $C_2$–$C_{10}$-alkynyl or $C_3$–$C_6$-cycloalkynyl, phenyl, naphthyl, or a five- to ten-membered saturated, partially unsaturated or aromatic heterocycle, containing one to four heteroatoms from the group consisting of O, N and S, $R^1$ and $R^2$ can also, together with the nitrogen atom to which they are bonded, form a five- or six-membered ring which can be interrupted by an atom from the group consisting of O, N and S and/or can carry one or more substituents from the group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1$–$C_4$-alkylene chain;

wherein $R^1$ and/or $R^2$ can be substituted by one to three identical or different groups $R^a$.

3. A compound of the formulae IIIa, IV and IVa

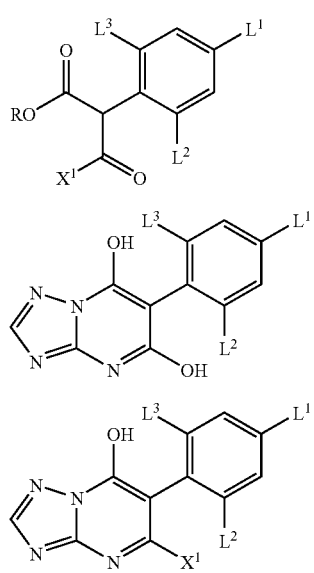

wherein
$L^1$ is $C_1$–$C_4$-alkyl;
$L^2$ is halogen;
$L^3$ is hydrogen or halogen;
R is $C_1$–$C_4$- alkyl; and
$X_1$ is $C_1$–$C_4$-alkyl.

4. A composition suitable for the control of harmful fungi, comprising a solid or liquid carrier and a compound of the general formula I as claimed in claim 1.

5. A method for the preparation of a composition suitable for the control of harmful fungi using the compound I as claimed in claim 1.

6. A method for the control of harmful fungi, which comprises treating the fungi or the materials, plants, ground or seeds to be protected from fungal attack with an effective amount of a compound of the general formula I as claimed in claim 1.

7. A process for the preparation of the compound of the formula I as claimed in claim 1 in which X is halogen, cyano, $C_1$–$C_4$-alkoxy or $C_1$–$C_2$-haloalkoxy, by reaction of 5-aminotriazole of the formula II

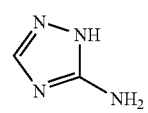

with phenylmalonates of the formula III,

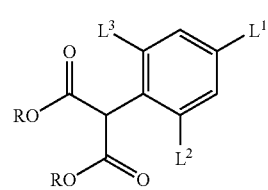

in which R is $C_1$–$C_6$-alkyl, to give dihydroxytriazolopyrimidines of the formula IV

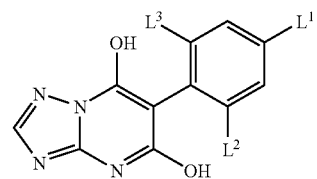

and halogenation to give the dihalogen compound of the formula V,

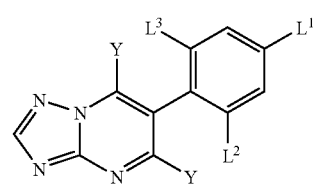

in which Y is halogen, reaction with amines of the formula VI,

in which $R^1$ and $R^2$ have the meanings given in claim 1, to give 5-halo-7-aminotriazolopyrimidines of the formula I in which x is halogen, and, for the preparation of compounds of the formula I in which x represents cyano, $C_1$–$C_4$-alkoxy or $C_1$–$C_2$-haloalkoxy, reaction with compounds of the formula VII,

M-X'     VII which, according to the meaning of the group X' to be introduced, represents an inorganic cyanide, alkoxide or haloalkoxide and in which M is an ammonium, tetraalkylammonium, alkali metal or alkaline earth metal cation.

8. A process for the preparation of the compound of the formula I as claimed in claim 1 in which X is $C_1$–$C_4$-alkyl, by reaction of 5-aminotriazole of the formula II as claimed in claim 3 with dicarbonyl compounds of the formula IIIa,

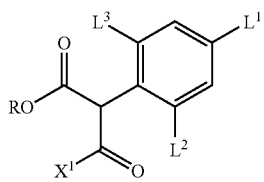

IIIa in which R and $X^1$ are $C_1$–$C_4$-alkyl, to give hydroxytriazolopyrimidines of the formula IVa

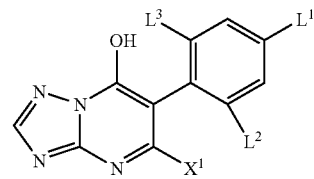

IVa halogenation to give compounds of the formula Va,

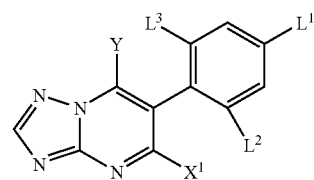

Va in which Y is halogen, and reaction with amines of the formula VI as claimed in claim 3 to give triazolopyrimidines of the formula I in which X is $C_1$–$C_4$-alkyl.

* * * * *

UNITED STATES PATENT AND TRADEMARK OFFICE
CERTIFICATE OF CORRECTION

PATENT NO. : 7,094,894 B2  Page 1 of 1
APPLICATION NO. : 10/513030
DATED : August 22, 2006
INVENTOR(S) : Blasco et al.

It is certified that error appears in the above-identified patent and that said Letters Patent is hereby corrected as shown below:

In Claim 1, col. 24, line 34: "$C_l$-$C_6$-haloalkyl" should read --$C_1$-$C_6$-haloalkyl--.

In Claim 2, col. 25, line 2: "10☐ring" should read --10-ring--.

In Claim 7, col. 26, line 42: "compound" should read --compounds--;
    col. 26, line 67: "x" should read --X--; and
    col. 27, line 1: "x" should read --X--.

In Claim 8, col. 27, line 14: "claim 3" should read --claim 7--; and
    col. 28, line 25: "claim 3" should read --claim 7--.

Signed and Sealed this

Seventeenth Day of April, 2007

JON W. DUDAS
*Director of the United States Patent and Trademark Office*